United States Patent
Tu et al.

(10) Patent No.: US 11,607,189 B2
(45) Date of Patent: Mar. 21, 2023

(54) METHOD AND APPARATUS FOR PROCESSING BLOOD VESSEL IMAGE, STORAGE MEDIUM, AND IMAGING DEVICE

(71) Applicant: Shanghai Pulse Medical Technology, Inc., Shanghai (CN)

(72) Inventors: Shengxian Tu, Shanghai (CN); Wei Yu, Shanghai (CN); Jiayue Huang, Shanghai (CN); Su Zhang, Shanghai (CN); Xiaogang Fu, Shanghai (CN)

(73) Assignee: SHANGHAI PULSE MEDICAL TECHNOLOGY, INC., Shanghai (CN)

( * ) Notice: Subject to any disclaimer, the term of this patent is extended or adjusted under 35 U.S.C. 154(b) by 224 days.

(21) Appl. No.: 17/250,441

(22) PCT Filed: Sep. 3, 2018

(86) PCT No.: PCT/CN2018/103798
§ 371 (c)(1),
(2) Date: Jan. 21, 2021

(87) PCT Pub. No.: WO2020/019408
PCT Pub. Date: Jan. 30, 2020

(65) Prior Publication Data
US 2021/0298706 A1    Sep. 30, 2021

(30) Foreign Application Priority Data
Jul. 24, 2018  (CN) .......................... 201810817666.4

(51) Int. Cl.
*G06K 9/00*    (2022.01)
*A61B 6/00*    (2006.01)
(Continued)

(52) U.S. Cl.
CPC ............ *A61B 6/504* (2013.01); *G06T 7/0014* (2013.01); *G06T 7/62* (2017.01); *G06T 11/001* (2013.01);
(Continued)

(58) Field of Classification Search
CPC ................................ G06T 2207/30048; G06T 2207/30101–30104; G06T 2207/30172;
(Continued)

(56) References Cited

U.S. PATENT DOCUMENTS

2014/0111541 A1\* 4/2014 Tolkowsky ............... G06T 7/62
  345/632
2015/0092999 A1\* 4/2015 Schmitt ................ A61B 6/5217
  382/128
(Continued)

FOREIGN PATENT DOCUMENTS

JP    2011024826 A    2/2011
JP    2015029566 A    2/2015
(Continued)

OTHER PUBLICATIONS

Japanese Office Action for Japanese Patent Application No. 503134/2021 dated Feb. 15, 2022.
(Continued)

*Primary Examiner* — Atiba O Fitzpatrick
(74) *Attorney, Agent, or Firm* — Maschoff Brennan

(57) ABSTRACT

The present invention relates to a blood vessel image processing method, a blood vessel image processing apparatus, a computer storage medium, and an imaging device. The method includes: obtaining blood vessel geometric structure information of a blood vessel segment of interest; obtaining vital feature information of the blood vessel segment; establishing an association relationship between the blood vessel geometric structure information and the
(Continued)

vital feature information; and displaying the blood vessel geometric structure information and the vital feature information in the same image in a mutual fusion manner by using the association relationship as a reference. In this way, work efficiency of users can be improved by the solution.

16 Claims, 6 Drawing Sheets

(51) Int. Cl.
    *G06T 7/62* (2017.01)
    *G06T 7/00* (2017.01)
    *G06T 11/00* (2006.01)
    *G06T 11/20* (2006.01)

(52) U.S. Cl.
    CPC .. *G06T 11/203* (2013.01); *G06T 2207/10072* (2013.01); *G06T 2207/20221* (2013.01); *G06T 2207/30016* (2013.01); *G06T 2207/30048* (2013.01); *G06T 2207/30101* (2013.01)

(58) Field of Classification Search
    CPC ... G06T 7/60; G06T 7/62; G06T 2207/20212; G06T 2207/20221; G06T 11/001; G06T 11/40; G06T 11/20–60; G06V 40/14–155; G06V 2201/12; G06V 30/414; G06V 30/186; G06V 30/18181
    See application file for complete search history.

(56) References Cited

U.S. PATENT DOCUMENTS

| | | | |
|---|---|---|---|
| 2015/0342537 A1* | 12/2015 | Taylor | A61B 5/743 600/508 |
| 2018/0082445 A1 | 3/2018 | Ishii et al. | |
| 2018/0092616 A1* | 4/2018 | Sakaguchi | A61B 6/032 |

FOREIGN PATENT DOCUMENTS

| | | |
|---|---|---|
| JP | 2015167790 A | 9/2015 |
| JP | 2017516535 A | 6/2017 |

OTHER PUBLICATIONS

Supplementary European search report dated Mar. 30, 2022 in European Patent Application No. 18927690.0.

Lee Kyung Eun et al: "A vessel length-based method to compute coronary fractional flow reserve from optical coherence tomography images Background", Biomedical Engineering Online, Jun. 26, 2017 (Jun. 26, 2017).

Ha Jinyong et al: "Assessing Computational Fractional Flow Reserve From Optical Coherence Tomography in Patients With Intermediate Coronary Stenosis in the Left Anterior Descending Artery", Journal of the American Heart Association, vol. 9, No. 8, Aug. 8, 2016 (Aug. 8, 2016).

Jang Sun-Joo et al: "Comparison of Accuracy of One-Use Methods for Calculating Fractional Flow Reserve by Intravascular Optical Coherence Tomography to That Determined by the Pressure-Wire Method", American Journal of Cardiology, vol. 120, No. 11, Sep. 1, 2017 (Sep. 1, 2017), pp. 1920-1925.

Tu Shengxian et al: "In Vivo Flow Simulation at Coronary Bifurcation Reconstructed by Fusion of 3-Dimensional X-ray Angiography and Optical Coherence Tomography", Journal of the American Heart Association, vol. 6, No. 2, Apr. 1, 2013 (Apr. 1, 2013), pp. 15-17.

Tenekecioglu Erhan et al: "Intracoronary optical coherence tomography: Clinical and research applications and intravascular imaging software overview : Intracoronary Optical Coherence Tomography", Catheterization and Cardiovascular Interventions, vol. 89, No. 4, Mar. 21, 2017 (Mar. 21, 2017).

Zafar Haroon et al: "Evaluation of hemodynamically severe coronary stenosis as determined by fractional flow reserve with frequency domain optical coherence tomography measured anatomical parameters", Journal of Cardiology, vol. 64, No. 1, Jul. 1, 2014 (Jul. 1, 2014), pp. 19-24.

Marmagkiolis Konstantinos et al: "Update on FFR, OCT, and IVUS", Imaging Cardiac Interventions Today, Oct. 31, 2014 (Oct. 31, 2014), pp. 37-40.

Pyxaras Stylianos A et al: "In-stent fractional flow reserve variations and related optical coherence tomography findings: the FFR-OCT co-registration study", International Journal of Cardiovascular Imaging, Kluwer Academic Publishers, Dordrecht, NL, vol. 34, No. 4, Oct. 27, 2017 (Oct. 27, 2017), pp. 495-502.

* cited by examiner

METHOD AND APPARATUS FOR PROCESSING BLOOD VESSEL IMAGE, STORAGE MEDIUM, AND IMAGING DEVICE

TECHNICAL FIELD

The present invention relates to the field of medical appliances, in particular to a blood vessel image processing method, a blood vessel image processing apparatus, a computer storage medium, and an imaging device.

BACKGROUND

A coronary ischemic heart disease is referred to as a coronary heart disease, and is a group of diseases that include stable angina, unstable angina, myocardial infarction and sudden death. For an ischemic heart disease, a conventional treatment method is mainly performing percutaneous coronary intervention (PCI) based on coronary angiography images to reconstruct a blood flow of the stenosis, to solve a downstream myocardium blood-supply problem. However, in fact, there is no fixed correspondence between whether myocardium is ischemia and the degree of vascular stenosis. Studies have shown that there is an error probability of one third between severity of stenosis judged by angiography and myocardial ischemia.

In many coronary artery physiological function assessment technologies, fractional flow reserve (FFR) is currently recognized as the most accurate functional assessment index. Moreover, FFR has become the gold standard for the clinical diagnosis of coronary heart disease, and is recommended by the European Society of Cardiology (ESC) guidelines as Ia level clinical evidence, and is recommended by the American College of Cardiology (ACC) guidelines as IIa level clinical evidence.

Currently, as far as the inventor knows, in the blood vessel image processing method, a guide wire or catheter with a pressure sensor is directly used to measure a FFR value of a blood vessel, and it is impossible to determine a correspondence between the FFR value and a specific point on the blood vessel segment; or a first image is used to show a relationship between blood vessel geometric structure information of the blood vessel and a distance, and a second image is used to show a relationship between vital feature information and a distance.

An applicant of the present invention has discovered, through a lot of experiments and research, that in the existing blood vessel image processing method, a relationship between the specifications of the two-dimensional sections of the blood vessel and a distance from any point on the blood vessel segment to the reference points and a relationship between the vital feature information of the blood vessel and the distance cannot be intuitively displayed at the same time.

Moreover, because of the defects, users of the blood vessel image processing apparatus have a problem of low work efficiency.

SUMMARY

The problem solved by the present invention is how to improve intuitiveness of blood vessel image processing to improve working efficiency of users.

To solve the above problem, an objective of the present invention is to provide a blood vessel image processing method, and the method includes: obtaining blood vessel geometric structure information of a blood vessel segment of interest; obtaining vital feature information of the blood vessel segment; establishing an association relationship between the blood vessel geometric structure information and the vital feature information; and displaying the blood vessel geometric structure information and the vital feature information in the same image in a fusion manner by using the association relationship as a reference.

Optionally, the establishing an association relationship between the blood vessel geometric structure information and the vital feature information includes: setting a reference position, and associating the vital feature information in the blood vessel segment with the blood vessel geometric structure information according to the reference position; where the blood vessel includes n two-dimensional sections, n two-dimensional sections correspond to n points on the blood vessel segment, and the reference position includes one of the following: a reference point, a reference section or a reference line, n≥1, and n is a positive integer.

Optionally, the displaying the blood vessel geometric structure information and the vital feature information in the same image in a mutual fusion manner by using the association relationship as a reference includes: establishing a first coordinate system, where an abscissa of the first coordinate system represents a distance from a point on the blood vessel segment to a preset reference position on the blood vessel segment, a first ordinate of the first coordinate system represents blood vessel geometric structure information of a blood vessel two-dimensional section corresponding to the point on the blood vessel segment, and an origin of the first ordinate is an intersection point of the abscissa and the first ordinate; for a preset number of two-dimensional sections of the blood vessel segment, determining a corresponding point according to the abscissa and the first ordinate of the first coordinate system, and drawing a first curve according to the determined point; and displaying the vital feature information in the blood vessel segment and the first curve in the same image in a mutual fusion manner.

Optionally, the displaying the vital feature information in the blood vessel segment and the first curve in the same image in a mutual fusion manner includes:

for a preset number of positions on the blood vessel segment, applying a false color to an area between the first curve, the abscissa of the first coordinate system, and the first ordinate, where there is a mapping relationship between the false color and the vital feature information of the two-dimensional section;

displaying the first curve, the false-colored area and the first coordinate system in the same image.

Optionally, the first coordinate system further includes: a second ordinate, the second ordinate represents vital feature information of each two-dimensional section, and an origin of the second ordinate is an intersection point between the abscissa and the second ordinate; and the displaying the vital feature information in the blood vessel segment and the first curve in the same image in a mutual fusion manner includes:

for a preset number of two-dimensional sections of the blood vessel segment, determining a corresponding point according to the abscissa of the first coordinate system and the second ordinate, and drawing a second curve according to the determined point; and displaying the first curve, the second curve and the first coordinate system in the same image.

Optionally, the displaying the vital feature information in the blood vessel segment and the first curve in the same image in a mutual fusion manner includes:

applying a false color to a curve determined by the vital feature information of n two-dimensional sections of the blood vessel and the abscissas, where there is a mapping relationship between the false color and the vital feature information of the two-dimensional section; and displaying the first curve, the false-colored curve determined by the vital feature information of n two-dimensional sections of the blood vessel and the abscissa, and the first coordinate system in the same image.

Optionally, the method further includes:

drawing a mirror-symmetric curve of the first curve as a third curve by using a straight line passing through the origin of the first ordinate and parallel to the abscissa as a central axis; where a longitudinal distance from the abscissa to the third curve is not less than zero; and displaying the vital feature information in the blood vessel segment, the first curve, and the third curve in the same image in a mutual fusion manner.

Optionally, the displaying the vital feature information in the blood vessel segment, the first curve, and the third curve in the same image in a mutual fusion manner includes:

for a preset number of points on the blood vessel segment, applying a false color to an area between the first curve, the third curve, and the first ordinate, where there is a mapping relationship between the false color and the vital feature information of the two-dimensional section; and displaying the first curve, the third curve, the false-colored area, and the first coordinate system in the same image.

Optionally, the first coordinate system further includes: a third ordinate, and the third ordinate represents vital feature information of each two-dimensional section, and an origin of the third ordinate is an intersection point of the abscissa and the third ordinate;

the displaying the vital feature information in the blood vessel segment, the first curve, and the third curve in the same image in a mutual fusion manner comprises:

for a preset number of points on the blood vessel segment, drawing a fourth curve according to the abscissa of the first coordinate system and the third ordinate;

drawing a mirror-symmetric curve of the fourth curve as a fifth curve by using a straight line passing through the origin of the third ordinate and parallel to the abscissa as a central axis; and displaying the first curve, the third curve, the fourth curve, and the fifth curve in the same image.

Optionally, the displaying the vital feature information in the blood vessel segment, the first curve, and the third curve in the same image in a mutual fusion manner includes:

for a preset number of points on the blood vessel segment, applying a false color to two curves determined by the vital feature information of the n two-dimensional sections of the blood vessel and the abscissas, where there is a mapping relationship between the false color and the vital feature information of the two-dimensional section, and the two curves are mirror-symmetric along the central axis.

Optionally, the blood vessel geometric structure information of the blood vessel segment includes at least one of the following: a diameter, a semidiameter, a cross-sectional area, or a major axis and a minor axis; and/or, the two-dimensional section of the blood vessel is a tangential section of the blood vessel; and/or, the vital feature information of each two-dimensional section of the blood vessel comprises at least one of the following: FFR information, a ratio of a distal pressure to a proximal pressure of the blood vessel or a pressure value; and/or, the blood vessel is a heart blood vessel, a peripheral blood vessel or a cerebral blood vessel.

Optionally, the method further includes:

when the blood vessel geometric structure information of the blood vessel segment is the major axis and the minor axis, filling an area between curves corresponding to the major axis and the minor axis with a preset color; and/or, displaying a narrowest point on the blood vessel segment in the same image; and/or, displaying a distal point and a proximal point on the blood vessel segment where the vital feature information is within a preset threshold range in the same image Optionally, the same image is a three-dimensional image, and the displaying the blood vessel geometric structure information and the vital feature information in the same image in a fusion manner by using the association relationship as a reference includes:

for any two-dimensional section on the blood vessel segment, applying a false color to a vascular wall of the blood vessel, where there is a mapping relationship between the false color and the vital feature information of the two-dimensional section in the blood vessel segment.

Optionally, the method further includes:

checking whether a viewing instruction of a user is received; and when the viewing instruction of the user is received, displaying the blood vessel geometric structure information and the vital feature information of the two-dimensional section of the blood vessel segment in which the user is interested.

Optionally, the obtaining vital feature information of a blood vessel segment of interest includes:

obtaining a coronary angiography image or a tomographic image of the blood vessel segment;

performing image processing on the coronary angiography image or the tomographic image of the blood vessel segment, where the image processing process at least comprises image segmentation and vascular lumen morphology reconstruction; and performing calculation on the vascular lumen morphology after segmentation and reconstruction to obtain the blood vessel geometric structure information of a lumen at each position on the reconstructed blood vessel segment, and obtaining vital feature information corresponding to each two-dimensional section by using a blood vessel pressure difference or a FFR calculation algorithm.

Optionally, the obtaining vital feature information of n two-dimensional sections of the blood vessel includes:

obtaining vital feature information of points on the blood vessel segment of interest by using a guide wire or a catheter with a pressure sensor; and making a correspondence between the vital feature information of each position point and a position on the blood vessel segment of interest according to a positioning component.

An embodiment of the present invention provides a blood vessel image processing apparatus, and the apparatus includes:

a first obtaining unit, configured to obtain blood vessel geometric structure information of a blood vessel segment of interest;

a second obtaining unit, configured to obtain vital feature information of the blood vessel segment;

an association unit, configured to establish an association relationship between the blood vessel geometric structure information and the vital feature information; and a display unit, configured to display the blood vessel geometric structure information and the vital feature information in the same image in a mutual fusion manner based on the association relationship.

Optionally, the association unit is configured to set a reference position, and associate the vital feature information in the blood vessel segment with the blood vessel geometric structure information according to the reference position; where the blood vessel includes n two-dimensional sections, the n two-dimensional sections correspond to n points on the blood vessel, and the reference position includes one of the following: a reference point, a reference section, or a reference line, n≥1, and n is a positive integer.

Optionally, the display unit includes:

a coordinate system creating subunit, configured to create a first coordinate system, where an abscissa of the first coordinate system represents a distance from a point on the blood vessel segment to a preset reference position on the blood vessel segment, a first ordinate of the first coordinate system represents blood vessel geometric structure information of a two-dimensional section of the blood vessel corresponding to a point on the blood vessel segment, and an origin of the first ordinate is an intersection point between the abscissa and the first ordinate;

a curve drawing subunit, configured to determine a corresponding point according to the abscissa and the first ordinate of the first coordinate system for a preset number of two-dimensional sections of the blood vessel segment, and drawing a first curve according to the determined point; and a display subunit, configured to display the vital feature information in the blood vessel segment and the first curve in the same image in a mutual fusion manner.

Optionally, the display subunit is configured to apply a false color to an area between the first curve, the abscissa of the first coordinate system and the first ordinate for a preset number of positions on the blood vessel segment, where there is a mapping relationship between the false color and the vital feature information of the two-dimensional section; and display the first curve, the false-colored area, and the first coordinate system in the same image.

Optionally, the first coordinate system further includes: a second ordinate, where the second ordinate represents vital feature information of each two-dimensional section, and an origin of the second ordinate is an intersection point of the abscissa and the second ordinate; and the display subunit is configured to determine a corresponding point according to the abscissa of the first coordinate and the second ordinate for a preset number of two-dimensional sections of the blood vessel segment, and draw a second curve according to the determined point; display the first curve, the second curve, and the first coordinate system in the same image.

Optionally, the display subunit is configured to apply a false color to a curve determined by the vital feature information of n two-dimensional sections of the blood vessel and the abscissas, where there is a mapping relationship between the false color and the vital feature information of the two-dimensional section; and display the first curve, the false-colored curve determined by the vital feature information of the n two-dimensional sections of the blood vessel and the abscissas, and the first coordinate system in the same image.

Optionally, the display subunit is further configured to draw a mirror-symmetric curve of the first curve as a third curve by use a straight line passing through the origin of the first ordinate and parallel to the abscissa as a center axis; where a longitudinal distance from the abscissa to the third curve is not less than zero; and the display subunit is further configure to display the vital feature information of the n two-dimensional sections of the blood vessel, the first curve, and the third curve in the same image in a mutual fusion manner.

Optionally, the display subunit is configured to apply a false color to an area between the first curve, the third curve and the first ordinate for a preset number of points on the blood vessel segment, where there is a mapping relationship between the false color and the vital feature information of the two-dimensional section; and display the first curve, the third curve, the false-colored area, and the first coordinate system in the same image.

Optionally, the first coordinate system further includes: a third ordinate, the third ordinate represents vital feature information of each two-dimensional section, and an origin of the third ordinate is an intersection point of the abscissa and the third ordinate;

the curve drawing subunit is further configured to draw a fourth curve according to the abscissa of the first coordinate system and the third ordinate for a preset number of points on the blood vessel segment; and draw a mirror-symmetric curve of the fourth curve as a fifth curve by using a straight line passing through the origin of the third ordinate and parallel to the abscissa as a central axis; and the display subunit is configured to display the first curve, the third curve, the fourth curve and the fifth curve in the same image.

Optionally, the display subunit is configured to apply, for a preset number of points on the blood vessel segment, a false color to two curves determined by the vital feature information of the n two-dimensional sections of the blood vessel and the abscissa, where there is a mapping relationship between the false color and the vital feature information of the two-dimensional section, and the two curves are mirror-symmetric along the central axis.

Optionally, the blood vessel geometric structure information of the blood vessel segment includes at least one of the following: a diameter, a semidiameter, a cross-sectional area, or a major axis and a minor axis; and/or, the two-dimensional section of the blood vessel is a tangential section of the blood vessel; and/or, the vital feature information of each two-dimensional section of the blood vessel includes at least one of the following: FFR information, a ratio of a distal pressure of the blood vessel to a proximal pressure or a pressure value; and/or, the blood vessel is a heart blood vessel, a peripheral blood vessel, or a cerebral blood vessel.

Optionally, the display subunit is further configured to: when the blood vessel geometric structure information of each two-dimensional section of the blood vessel is the major axis and the minor axis, fill an area between curves corresponding to the major axis and the minor axis with a preset color; and/or, the display subunit is further configured to: display a narrowest point on the blood vessel segment in the same image; and/or, display, in the same image, a distal end point and a proximal end point on the blood vessel segment where the vital feature information is within a preset threshold range.

Optionally, the same image is a three-dimensional image, and the display unit is configured to apply a false color to a lumen wall of the blood vessel for any two-dimensional section on the blood vessel segment, where there is a mapping relationship between the false color and the vital feature information of the two-dimensional section.

Optionally, the apparatus further includes:

a checking unit, configured to check whether a viewing instruction of a user is received; where the display unit is further configured to display the blood vessel geometric structure information and vital feature information of the two-dimensional section of the blood vessel segment in which the user is interested when the checking unit receives the viewing instruction of the user.

Optionally, the second obtaining unit is configured to:

obtain a coronary angiography image or a tomographic image of the blood vessel; perform image processing on the coronary angiography image or the tomographic image of the blood vessel, where the image processing process includes at least image segmentation and vascular lumen morphology reconstruction; perform calculation on the vascular lumen morphology after segmentation and reconstruction to obtain the vascular geometric structure information of a lumen at each position of the reconstructed blood vessel, and obtain the vital feature information corresponding to each two-dimensional section by using a blood vessel pressure difference or a FFR calculation algorithm.

Optionally, the second obtaining unit is configured to obtain vital feature information of points on the blood vessel segment of interest by using a guide wire or a catheter with a pressure sensor; and making a correspondence between the vital feature information of each position point and a position on the blood vessel segment of interest according to a positioning component.

An embodiment of the present invention provides a computer storage medium on which a computer program that can be run on a processor is stored, and the computer program implements the blood vessel image processing method according to any one of the possible implementations when being executed by the processor.

An embodiment of the present invention provides an imaging device, including the blood vessel image processing apparatus according to any one of the possible implementations.

Optionally, the imaging device includes any one of the following: an angiography machine, an X-ray computed tomography camera, an intravascular ultrasound imaging device, and an optical coherence tomography imaging device.

Compared with the prior art, the blood vessel image processing method and the blood vessel image processing apparatus provided by the present invention have the following advantages:

In the blood vessel image processing method of the present invention, an association relationship between the blood vessel geometric structure information and the vital feature information is established, and then the blood vessel geometric structure information and the vital feature information are displayed in the same image in a mutual fusion manner by using the association relationship as a reference. A user of the blood vessel image processing apparatus, especially a doctor user, can directly and simultaneously see vital feature information and blood vessel geometric structure information at any position on a blood vessel segment by viewing an image, and can see vital feature information of which segment of the blood vessel has a larger decline from a proximal end to a distal end of the blood vessel segment of interest. There is no need for the doctor to compare two images that are a first image and a second image to view the vital feature information and the blood vessel geometric structure information of any point or two-dimensional section of the blood vessel segment. Therefore, it is convenient for the doctor user to diagnose a disease of a patient, and it is further convenient for the doctor user to determine a treatment plan of the disease. In this way, work efficiency of the user can be improved.

Further, a first curve representing the change of the blood vessel geometric structure information of the two-dimensional section of the blood vessel is drawn by establishing a first coordinate system, and a false color is applied to an area between the first curve and the abscissa of the first coordinate system, and there is specifically a mapping relationship between the false color and the vital feature information of the two-dimensional section of the blood vessel. For example, red can correspond to that FFR of the two-dimensional section of the blood vessel is 0.6. Therefore, the user can make the diagnosis of the disease quickly by viewing an image. In this way, work efficiency of the doctor can be improved.

Further, the blood vessel geometric structure information of the two-dimensional section of the blood vessel are set to be the major axis and the minor axis, and an area between curves corresponding to the major axis and the minor axis is filled with a preset color. In this way, in an image, the user can not only view the size of the blood vessel, but also view the eccentricity of the two-dimensional section of the blood vessel, thereby improving accuracy of the diagnosis of the disease made by the user.

Further, a narrowest point on the blood vessel segment is displayed in the same image, and then that the doctor user can determine the worst condition of the blood vessel at a relatively fast speed, so that the time of the doctor user is saved.

Further, because the blood vessel image processing apparatus can display the blood vessel geometric structure information and the vital feature information of the two-dimensional section the blood vessel segment in which the user is interested when receiving a viewing instruction of the user. Therefore, the user can move, according to personal needs, a mouse to any interested position on the blood vessel segment to view the blood vessel geometric structure information and vital feature information. In this way, user experience can be improved.

In order to make the above content of the present invention more obvious and understandable, preferred embodiments are described in detail below with reference to the accompanying drawings.

DETAILED DESCRIPTION OF EMBODIMENTS

Figure 1:
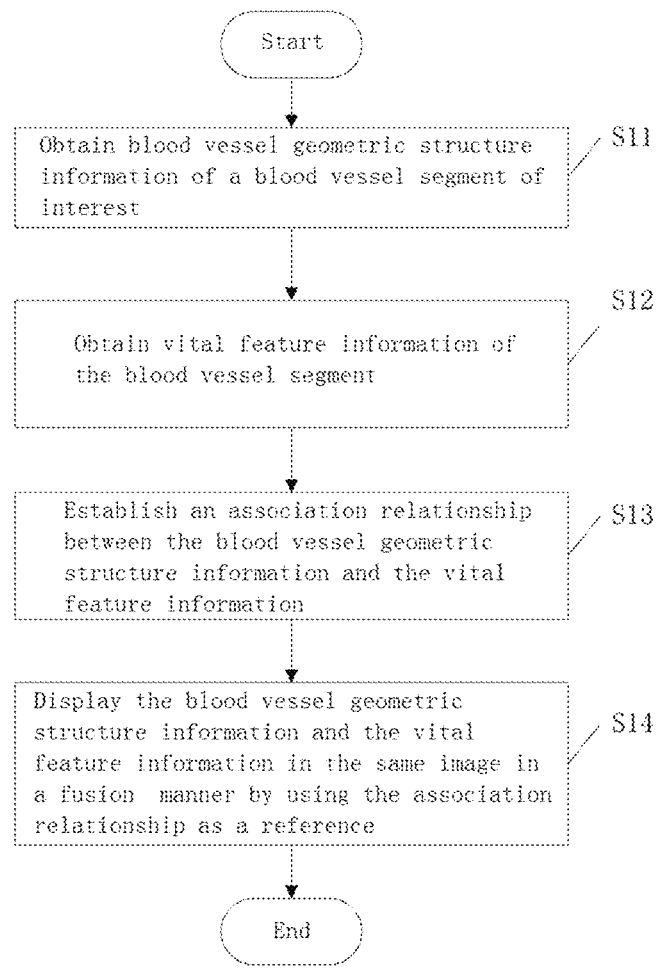
FIG. 1 is a schematic flowchart of a blood vessel image processing method according to an embodiment of the present invention.

The following specific embodiments illustrate the implementation of the present invention, and a person skilled in the art can easily understand other advantages and effects of the present invention from the content disclosed in the description. Although the description of the present invention is introduced with reference to the preferred embodiments, it does not indicate that the features of the present invention are limited to the implementation. On the contrary, an objective of introducing the present invention with reference to the embodiments is to cover other options or modifications that may be extended based on the claims of the present invention. In order to provide an in-depth understanding of the present invention, many specific details are included in the following description. The present invention can also be implemented without using these details. In addition, in order to avoid confusion or obscuring the focus of the present invention, some specific details are omitted in the description. It should be noted that the embodiments of the present invention and the features in the embodiments can be combined with each other if there is no conflict.

In many coronary artery physiological function assessment technologies, fractional flow reserve (FFR) is currently recognized as the most accurate functional assessment index. Moreover, FFR has become the gold standard for the clinical diagnosis of coronary heart disease, is recommended by the European Society of Cardiology (ESC) guidelines as Ia level clinical evidence, and is recommended by the American College of Cardiology (ACC) guidelines as Ha level clinical evidence.

However, the conventional blood vessel image processing method has a problem that work efficiency of a user of the blood vessel image processing apparatus is low.

In order to solve the problem, embodiments of the present invention provide a blood vessel image processing method. An association relationship between the blood vessel geometric structure information and the vital feature information is established, and then the blood vessel geometric structure information and the vital feature information are displayed in the same image in a mutual fusion manner by using the association relationship as a reference. A user of the blood vessel image processing apparatus, especially a doctor user, can directly and simultaneously see vital feature information and blood vessel geometric structure information at any position on a blood vessel segment by viewing an image. There is no need for the doctor to compare two images that are a first image and a second image to view the vital feature information and the blood vessel geometric structure information of any point or two-dimensional section of the blood vessel segment. Therefore, it is convenient for the doctor user to diagnose a disease of a patient, and it is further convenient for the doctor user to determine a treatment plan of the disease. In this way, work efficiency of the user can be improved.

The present invention is explained in detail below with reference to the drawings.

FIG. 1 is a schematic flowchart of a blood vessel image processing method according to an embodiment of the present invention. As shown in FIG. 1, the method may include the following steps:

Step S11: Obtain blood vessel geometric structure information of a blood vessel segment of interest.

It should be noted that a blood vessel is generally a tubular cavity. If the blood vessel is divided, a blood vessel segment can be divided into n segments, that is, the blood vessel can include n two-dimensional sections. Correspondingly, there are n divisions on the blood vessel segment, that is, n two-dimensional sections can correspond to n points on the blood vessel segment.

In a specific implementation, the blood vessel geometric structure information may include at least: blood vessel geometric structure information of each two-dimensional section of the blood vessel. In detail, the blood vessel geometric structure information may include at least one of the following: a diameter, a semidiameter, a cross-sectional area, or a major axis and a minor axis. Specifically, the blood vessel geometric structure information may include only the diameter, or may include only the semidiameter, or may include only the cross-sectional area, or may include only the major axis and the minor axis, or the blood vessel geometric structure information of each two-dimensional section may include a combination of the various situations, for example, the blood vessel geometric structure information of the two-dimensional section may include the diameter and the cross-sectional area, or may include the diameter, and the major axis and the minor axis.

It should be noted that, because a blood vessel is not standard circle in general, but an ellipse, in order to clarify specifications of the two-dimensional section of the blood vessel, there may be two parameters: the major axis and the minor axis of the lumen. That is to say, in an embodiment of the present invention, specification parameters need to include both the major axis and the minor axis, and the major axis and the minor axis of the two-dimensional section of the blood vessel are used to represent specifications of the blood vessel. In this way, it may be not only convenient for the user to understand the specification of the blood vessel, and but also convenient for the user to know an eccentricity of the blood vessel. Therefore, it may be convenient for the user, especially the doctor user, to diagnose and treat a disease and determine a treatment plan.

Moreover, because the blood vessel is not a standard circle in general, but an ellipse, the diameter and the semidiameter mentioned in the embodiments of the present invention are an equivalent diameter and an equivalent semidiameter. Regarding the equivalent diameter, specifically, for a section of any blood vessel segment, an area of the section can be calculated, and assuming that the cross section of the blood vessel segment is a circle, a diameter corresponding to this circle can be calculated, the calculated diameter is the equivalent diameter. Similarly, assuming that the cross section of the blood vessel segment is a circle, a corresponding semidiameter is calculated, and the calculated semidiameter is the equivalent semidiameter.

In an embodiment of the present invention, the blood vessel may be a heart blood vessel, a peripheral blood vessel or a cerebral blood vessel, and that the blood vessel is the heart blood vessel is used as an example to describe the following embodiments. A person skilled in the art can also use the solutions in the embodiments of the present invention for blood vessels in other parts according to actual needs.

In an embodiment of the present invention, the two-dimensional section of the blood vessel may be a tangential section of the blood vessel, that is, the two-dimensional section of the blood vessel is a two-dimensional section obtained by cutting the blood vessel in a vertical direction, so that it is convenient for the user to view.

Step S12: Obtain vital feature information in the blood vessel segment.

In a specific implementation, the vital feature information of each two-dimensional section of the blood vessel refers to information that can represent the disease or working condition of the blood vessel. For example, the vital feature information may include at least one of the following: FFR information, a ratio of a distal pressure of the blood vessel to a proximal pressure or a pressure value. Specifically, the vital feature information of the two-dimensional section may be the FFR information, may be the ratio of the distal pressure of the blood vessel to the proximal pressure, or may be the pressure value, and may further be any combination of two or even three of the following: the FFR information, the ratio of the distal pressure of the blood vessel to the proximal pressure, or the pressure value.

In a specific implementation, the vital feature information of the two-dimensional section can be obtained in multiple manners.

In an embodiment of the present invention, in order to obtain the vital feature information of the n two-dimensional sections of the blood vessel, the following steps may be performed: Firstly, a coronary angiography image or a tomographic image of the blood vessel is obtained, and then image processing is performed on the coronary angiography image or the tomographic image of the blood vessel. The image processing process specifically includes at least image segmentation and vascular lumen morphology reconstruction, and then calculation is performed on the vascular lumen morphology after segmentation and reconstruction to obtain the blood vessel geometric structure information of a lumen at each position of the reconstructed blood vessel, and a blood vessel pressure difference or a FFR calculation algorithm is used to obtain the corresponding vital feature information at each two-dimensional section. It should be noted that the above FFR calculation algorithm may be an algorithm conventionally obtained by the person skilled in the art. Details are not repeated herein. In addition, there may be multiple specific imaging manners and principles, such as an X-ray imaging principle, a CT imaging principle, an intravascular ultrasound imaging principle, or an optical coherence tomography imaging principle.

In order to reduce costs, in another embodiment of the present invention, a positioning component can be provided on a guidewire or catheter with a pressure sensor, and then the conventional guidewire or catheter with the pressure sensor and the positioning component can be used to obtain the vital feature information of points on the blood vessel segment of interest, and then make a correspondence between the vital feature information of each position point and the two-dimensional section of the blood vessel of interest. For example, a position sensor can be installed on a guidewire or catheter with a pressure sensor. When the guidewire or catheter with a pressure sensor detects the vital feature information of a certain point on the blood vessel segment, the position sensor correspondingly locates a certain point on the blood vessel segment. Therefore, a correspondence between the vital feature information of each position point and the two-dimensional section of the blood vessel of interest can be made.

It should be noted that the embodiment of the present invention does not limit the sequence of step S11 and step S12, and step S12 may be performed first, and then step S11 may be performed.

Step S13: Establish an association relationship between the blood vessel geometric structure information and the vital feature information.

Regarding the establishment of an association relationship between the blood vessel geometric structure information and the vital feature information, in a specific implementation, a reference position may be set first, and then the vital feature information in the blood vessel segment and the blood vessel geometric structure information may be associated according to the reference position. The reference position may include various forms. For example, the reference position may be a reference point, a reference section, or a reference line.

In an embodiment of the present invention, the reference point can be selected as the reference position. For ease of description, a distance from the point on the blood vessel segment to the preset reference point on the blood vessel segment can be referred to as x, where n≥1, Y≥x≥0, and y represents the length of the blood vessel of interest. In a specific implementation, the preset reference point on the blood vessel segment may be a proximal end of the blood vessel, may be a distal end of the blood vessel, or may be other end points selected by the person skilled in the art according to actual needs.

In a specific implementation, a specific execution order of steps S11, S12, and S13 is not strictly limited. The above three steps can be performed alternately provided that the association relationship between the blood vessel geometric structure information and the vital feature information is finally established. For example, the blood vessel geometric structure information of the blood vessel segment of interest can be obtained first, the reference position can further be obtained by division, and then the vital feature information in the blood vessel segment associated with any position on the blood vessel segment can be obtained according to the reference position. For example, the vital feature information of the blood vessel segment of interest can be obtained first, the reference position can further be obtained by division, and then the blood vessel geometric structure information in the blood vessel segment associated with any position on the blood vessel segment can be obtained according to the reference position. For another example, the blood vessel geometric structure information and the vital feature information of the blood vessel segment may be obtained separately in any order, and then the blood vessel geometric structure information and the vital feature information are correspondingly associated according to the reference position.

Step S14: Display the blood vessel geometric structure information and the vital feature information in the same image in a mutual fusion manner by using the association relationship as a reference.

In a specific implementation, when a reference point is used, the vital feature information of the n two-dimensional sections of the blood vessel, the blood vessel geometric structure information of the n two-dimensional sections of the blood vessel, and a distance x from a point corresponding to each of the two-dimensional sections to the preset reference point on the blood vessel segment are displayed in the same image in a mutual fusion manner.

In a specific implementation, in order to display the blood vessel geometric structure information and the vital feature information in the same image in a mutual fusion manner by using the association relationship a reference, a coordinate system can be established first. For ease of description, the established coordinate system can be referred to as a first coordinate system. An abscissa of the first coordinate system can represent a distance x from a point on the blood vessel segment to a preset reference point on the blood vessel segment. A first ordinate of the first coordinate system can represent blood vessel geometric structure information of each two-dimensional section. An origin of the first ordinate can be an intersection point of the abscissa and the first ordinate. For the preset number of two-dimensional sections of the blood vessel segment, that is, a certain number of sampling points on the blood vessel segment, corresponding points can be determined according to the abscissa and the first ordinate of the first coordinate system, the corresponding points are connected, and then the first curve is obtained by drawing. Then, the vital feature information of the n two-dimensional sections of the blood vessel and the first curve are displayed in the same image in a mutual fusion manner. It should be noted that the person skilled in the art can set the specific preset number according to actual needs provided that the first curve can be drawn according to the corresponding points.

Moreover, when the blood vessel geometric structure information is the major axis and the minor axis, because there are two dimensions that are the major axis and the minor axis, the first curve drawn above may specifically include two curves. For ease of understanding, the two curves are respectively referred to as a first sub-curve and a second sub-curve. The first sub-curve may be a curve that represents the change of the major axis of the two-dimensional section of the blood vessel, and the second sub-curve may be a curve that represents the change of the minor axis of the two-dimensional section of the blood vessel. Regarding the blood vessel geometric structure information and the vital feature information are displayed in the same image in a mutual fusion manner by using the association relationship as a reference, the vital feature information of the two-dimensional section, the first sub-curve, and the second sub-curve are displayed in one image in a mutual fusion manner.

In a specific implementation, various ways can be used to display the vital feature information and the first curve representing the geometric structure information of the blood vessel can be displayed in the same image in a mutual fusion manner.

In an embodiment of the present invention, for the preset number of points on the blood vessel segment, a false color having a mapping relationship with the vital feature information of the two-dimensional section may be applied to an area between the first curve and the abscissa and the ordinate of the first coordinate system, and further the first curve, the false-colored area, and the first coordinate system can be displayed in the same image.

Figure 2:
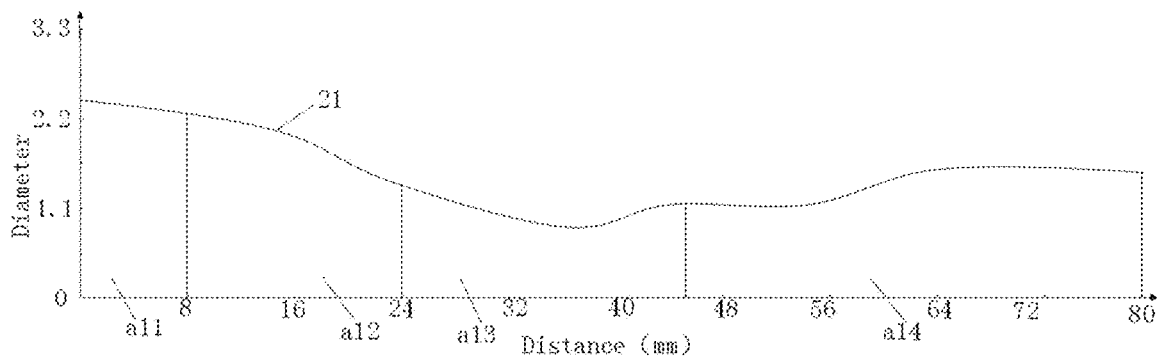
FIG. 2 is a schematic diagram of displaying a blood vessel image according to an embodiment of the present invention.

For ease of understanding, as an example only, referring to FIG. 2, FIG. 2 is a way of displaying a blood vessel image according to an embodiment of the present invention. As shown in FIG. 2, an abscissa represents a distance x, an ordinate represents a diameter, and vital feature information is FFR information. A first curve 21 represents a correspondence between the distance x and the diameter. For example, the distance x=8 mm, the diameter of a two-dimensional section of a blood vessel is 2.0 mm, and for an area formed by the abscissa, the ordinate and the first curve 21, in an area a11 of a segment x∈(0,8), an applied false color may be a first color, and the corresponding FFR=0.8; in an area a12 of a segment x∈(8,24), an applied false color can be a second color, and the corresponding FFR=0.6; in an area a13 of a segment x∈(24,45), an applied false color may be a third color, and the corresponding FFR=0.56; in an area a14 of a segment x∈(45,78), an applied false color can be a fourth color, and the corresponding FFR=0.48. Certainly, in practical applications, there may be a color transition at the junction of two colors. This is not shown in FIG. 2 herein.

Therefore, the user needs to view only an image including a first coordinate system, such as FIG. 2, and can intuitively see both the diameter of a two-dimensional section and the FFR information for any point on the blood vessel segment. For example, if the user is interested in a point at which x=10 mm, it can be learned, in the first coordinate system, that the diameter of a two-dimensional section of the blood vessel is 1.8 mm by using the first curve 21, and it can be determine that the FFR=0.6 of the blood vessel by using the second color. Therefore, the doctor user can diagnose a disease and determine a treatment plan.

In an embodiment of the present invention, when the blood vessel geometric structure information is the major axis and the minor axis, there is an applied false color that has a mapping relationship with the vital feature information of the two-dimensional section.

Specifically, a false color that has a mapping relationship with the vital feature information of the two-dimensional section is applied to an area between the second sub-curve, and the abscissa and the ordinate of the first coordinate system, and the first sub-curve, the second sub-curve, the false-colored area, and the first coordinate system are displayed in the same image.

Figure 3:
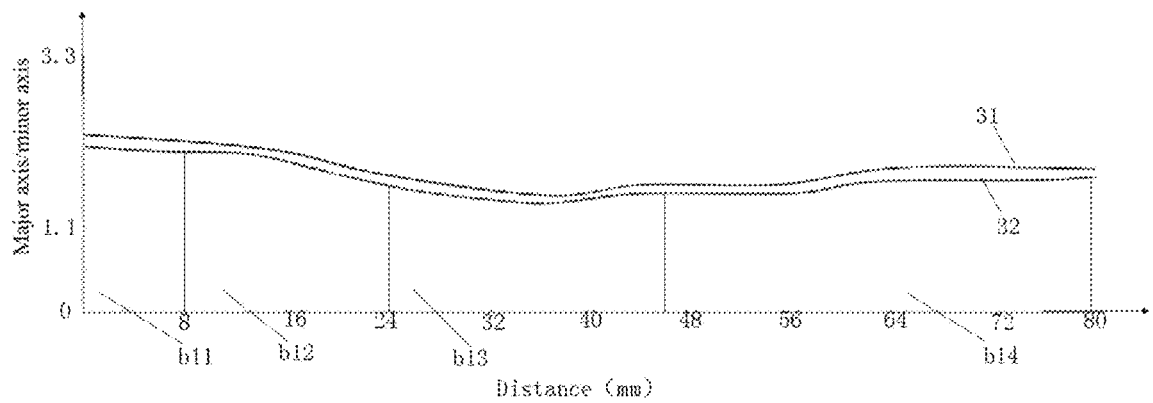
FIG. 3 is a schematic diagram of displaying a blood vessel image according to an embodiment of the present invention.

For ease of understanding, referring to FIG. 3, as shown in FIG. 3, an abscissa represents a distance x, an ordinate represents a major axis and a minor axis, vital feature information is FFR information. A first sub-curve 31 represents a correspondence between the distance x and the major axis. A second sub-curve 32 represents a correspondence between the distance x and the minor axis. For example, the distance x=8 mm, the diameter of a two-dimensional section of the blood vessel is 2.0 mm. For an area b formed by the abscissa, the ordinate, and the second sub-curve 32, in an area b11 of a segment x∈(0,8), an applied false color may be a first color, and the corresponding FFR=0.8; in an area b12 of a segment x∈(8,24), an applied false color may be a second color, and the corresponding FFR=0.6; in an area b13 of x∈(24,45), an applied false color may be a third color, and the corresponding FFR=0.54; in an area b14 of a segment x∈(45,78), an applied false color may be a fourth color, and the corresponding FFR=0.43. Certainly, in practical applications, there may be a color transition at the junction of two colors. This is not shown in FIG. 3 herein.

Therefore, the user needs to view only an image including a first coordinate system, such as FIG. 3, and can intuitively see the major axis and the minor axis, and the FFR information of a two-dimensional section for any point on the blood vessel segment. For example, if the user is interested in a point at which x=10 mm, it can be learned, in the first coordinate system, that the major axis of the two-dimensional section of the blood vessel is 2.1 mm by using the first sub-curve 31, and the minor axis of the two-dimensional section of the blood vessel is 1.6 mm by using the second sub-curve 32, and it can be determined that the FFR=0.6 of the blood vessel by using the second color. Therefore, the doctor user can diagnose a disease and determine a treatment plan.

In a specific implementation, when the blood vessel geometric structure information of each two-dimensional section of the blood vessel is the major axis and the minor axis, an area between the curves corresponding to the major axis and the minor axis can further be filled with a preset color. The user can more intuitively see the difference between the major axis and the minor axis of the two-dimensional section of the blood vessel, can quickly determine the degree of malformation or an eccentricity of the blood vessel. Therefore, information of the blood vessel can be intuitively displayed and working efficiency of the user can be improved.

It should be noted that, in a specific implementation, the person skilled in the art can select the preset color according to actual needs, and the specific color does not constitute any limitation to the present invention. For ease of understanding, referring to FIG. 4, an abscissa represents a distance x, an ordinate represents a major axis and a minor axis, and vital feature information is FFR information. A first sub-curve 41 represents a correspondence between the distance x and the major axis. A second sub-curve 42 represents a correspondence between the distance x and the minor axis. An area 40 between the first sub-curve 41 and the second sub-curve 42 is filled with gray.

Figure 4:
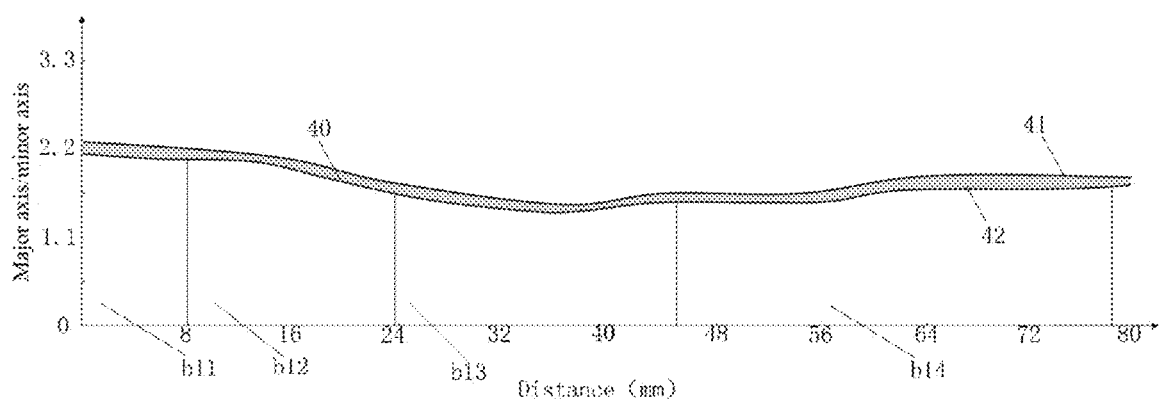
FIG. 4 is a schematic diagram of displaying a blood vessel image according to an embodiment of the present invention.

Therefore, the user needs to view only an image including a first coordinate system, such as FIG. 4, and can intuitively see the major axis, the minor axis and the FFR information of a two-dimensional section for any point on the blood vessel segment. For example, if the user is interested in a point at which x=10 mm, it can be learned, in the first coordinate system, that the major axis of the two-dimensional section of the blood vessel is 2.1 mm by using the first sub-curve 41, and the minor axis of the two-dimensional section of the blood vessel is 1.6 mm by using the second sub-curve 42, it can be determined that the FFR=0.6 of the blood vessel by using the second color, and it can be further learned that an eccentricity of the blood vessel is the largest near x=40 mm Therefore, it is convenient for the doctor user to diagnose a disease and determine a treatment plan. It should be noted that, except that an area 40 between the first sub-curve 41 and the second sub-curve 42 is filled with gray, the person skilled in the art can refer to FIG. 3 to implement the other parts in FIG. 4. Details are not described herein.

It should be noted that the person skilled in the art can preset a mapping relationship between the vital feature information and the false color according to actual needs. In an embodiment of the present invention, the mapping relationship between vital feature information and the false color can be shown in Table 1 below. Referring to Table 1, when FFR<0.8, the false color can change from orange to red to warn that a stent needs to be placed at the blood vessel. When FFR>0.8, the false color is blue to indicate that there is no obvious myocardial ischemia. Certainly, no limitation is set on the specific mapping relationship in the present invention. In other words, the specific mapping relationship does not constitute any limitation on the protection scope of the present invention.

TABLE 1

| FFR | RGB |
| --- | --- |
| 0.0 | 255, 0, 0 |
| 0.1 | 255, 0, 0 |
| 0.2 | 255, 0, 0 |
| 0.3 | 255, 0, 0 |
| 0.4 | 255, 11, 0 |
| 0.5 | 255, 24, 0 |
| 0.6 | 255, 37, 0 |
| 0.7 | 255, 50, 0 |
| 0.8 | 255, 173, 0 |

TABLE 1-continued

| FFR | RGB |
| --- | --- |
| 0.9 | 51, 255, 0 |
| 1.0 | 0, 51, 255 |

In another embodiment of the present invention, the first coordinate system may further include: a second ordinate. The second ordinate represents vital feature information of each two-dimensional section, and an origin of the second ordinate is an intersection point of the abscissa and the second ordinate. Therefore, the two ordinates share the same abscissa to display the first curve and the vital feature information in a mutual fusion manner. Specifically, for a preset number of two-dimensional sections of the blood vessel segment, that is, a preset number of sampling points on the blood vessel, corresponding points can be determined according to the abscissa of the first coordinate system and the second ordinate, then a second curve is obtained according to the determined points, and the first curve, the second curve and the first coordinate system are further displayed in the same image.

Figure 5:
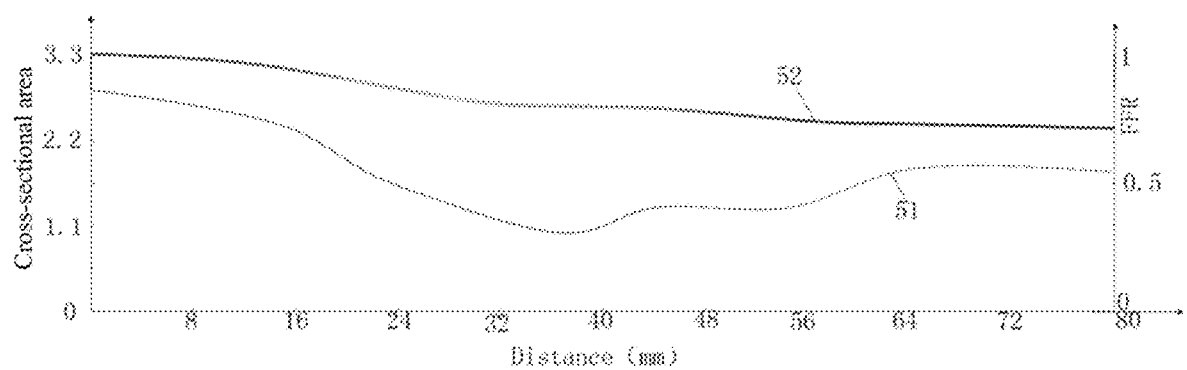
FIG. 5 is a schematic diagram of displaying a blood vessel image according to an embodiment of the present invention.

For ease of understanding, refer to FIG. 5 for details. As shown in FIG. 5, an abscissa represents a distance x, a first ordinate, that is, an ordinate on the left represents a cross-sectional area, and a second ordinate, that is, an ordinate on the right represents FFR information. A first curve 51 represents a correspondence between the distance x and the cross-sectional area. For example, the distance x=8 mm, and the cross-sectional area of the two-dimensional section of the blood vessel is 4.0. A second curve 52 represents a correspondence between the distance x and the FFR. For example, the distance x=8 mm, and the FFR of the two-dimensional section of the blood vessel is 0.92. Therefore, the user needs to view only an image including the first coordinate system, can intuitively see both the cross-sectional area and the FFR information of a two-dimensional section for any point on the blood vessel segment, and can further see the FFR of which segment of the blood vessel has a larger decline from a proximal end to a distal end. For example, if the user is interested in a point at which x=10 mm, it can be learned, in the first coordinate system, that the cross-sectional area of the two-dimensional section of the blood vessel is 4.0 by using the first curve 51, and it can be determined that the FFR=0.92 of the blood vessel by using the second curve 52. The above information is information that clinicians are more concerned about. Therefore, it is convenient for the doctor user to diagnose a disease and determine a treatment plane by using the blood vessel image processing method in the embodiment of the present invention.

In another embodiment of the present invention, in order to display the vital feature information and the first curve in the same image, a false color may be applied to the curve determined by the vital feature information of the n two-dimensional sections of the blood vessel and the abscissa, where there is a mapping relationship between the false color and the vital feature information of the two-dimensional section, and then the first curve, the false-colored curve determined by the vital feature information of the n two-dimensional sections of the blood vessel and the abscissa, and the first coordinate system are displayed in the same image.

Figure 6:
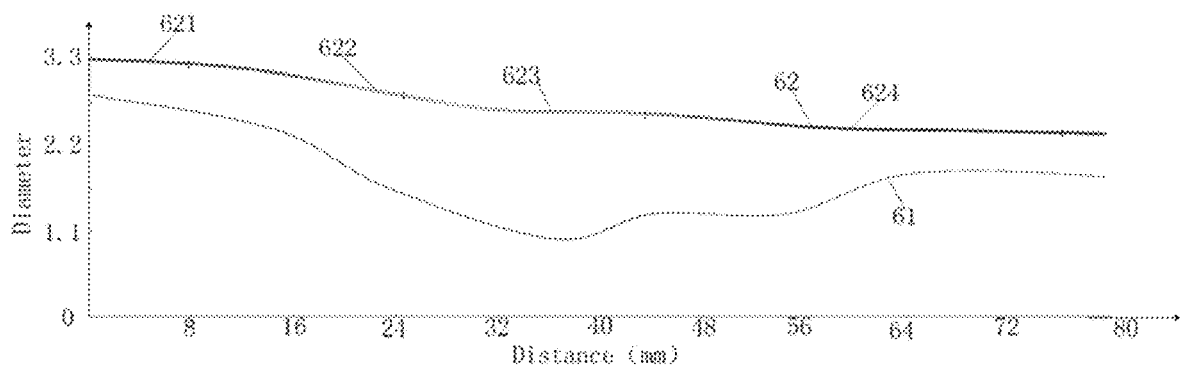
FIG. 6 is a schematic diagram of displaying a blood vessel image according to an embodiment of the present invention.

For ease of understanding, refer to FIG. 6 for details. As shown in FIG. 6, an abscissa represents a distance x, and an ordinate represents a diameter. A first curve 61 represents a correspondence between the distance x and the diameter. For example, the distance x=8 mm, and the diameter of the two-dimensional section of the blood vessel is 4.0. For a curve 62 determined according to a correspondence between the vital feature information of the two-dimensional section and the point on the blood vessel segment, in a curve segment 621 of the abscissa x∈(0,8), an applied false color may be a first color, and the corresponding FFR=0.8; in a curve segment 622 of x∈(8,24), an applied false color may be a second color, and the corresponding FFR=0.6; in a curve segment 623 of x∈(24,45), an applied false color may be a third color, and the corresponding FFR=0.54; in a curve segment 624 of x∈(45,78), an applied false color can be a fourth color, and the corresponding FFR=0.43.

Certainly, in practical applications, there may be a color transition at the junction of the two colors. As it is understandable, no more details are shown in FIG. 6 herein. Therefore, the user needs to view only an image including the first coordinate system, such as FIG. 6, and can intuitively see both the diameter and the FFR information of a two-dimensional section for any point on the blood vessel segment. For example, if the user is interested in a point at which x=10 mm, it can be learned, in the first coordinate system, that the diameter of the two-dimensional section of the blood vessel is 1.8 mm by using the first curve 61, and it can be determined that the FFR=0.6 of the blood vessel by using the second color in the curve segment 622 of x∈(8,24) of the curve 62. Therefore, it is convenient for the doctor user to diagnose a disease and determine a treatment plan.

Because the shape of the cross section of the blood vessel is usually elliptical, in a specific implementation, a mirror-symmetric curve of the first curve can be drawn as a third curve by using a straight line passing through the origin of the first ordinate and parallel to the abscissa can be used as a central axis. A longitudinal distance from the abscissa to the ordinate of the third curve is not less than zero, that is, the abscissa is lower than the third curve, and the vital feature information of the n two-dimensional sections of the blood vessel, the first curve, and the third curve are displayed in the same image in a mutual fusion manner. Therefore, the first curve, the third curve, and an area formed between the two can form a simulated shape of the two-dimensional section of the blood vessel, and the simulated shape can be closer to the shape of the cross section of the blood vessel, so that the specifications of the blood vessel can be displayed more intuitively.

In a specific implementation, the vital feature information of the n two-dimensional sections of the blood vessel, the first curve, and the third curve are displayed in the same image in a mutual fusion manner. Specifically, for a preset number of points on the blood vessel segment, a false color is applied to an area between the first curve, the third curve, and the first ordinate, where there is a mapping relationship between the false color and the vital feature information of the two-dimensional section, and then the first curve, the third curve, the false-colored area, and the first coordinate system are displayed in the same image.

Figure 7:
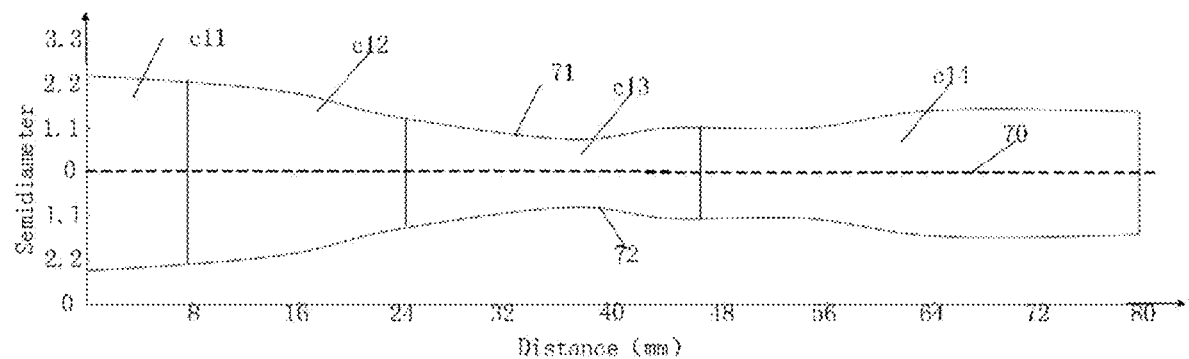
FIG. 7 is a schematic diagram of displaying a blood vessel image according to an embodiment of the present invention.

For ease of understanding, referring to FIG. 7, FIG. 7 is a way of displaying a blood vessel image according to an embodiment of the present invention. As shown in FIG. 7, an abscissa represents a distance x, an ordinate represents a semidiameter, and vital feature information is FFR information. A first curve 71 and a third curve 72 can both represent a correspondence between the distance x and the diameter. The first curve 71 and the third curve 72 are mirror-symmetric curves with respect to a central axis 70, and the central axis 70 is parallel to the abscissa. For example, the distance x=8 mm, the diameter of the two-dimensional section of the blood vessel is 2.0 mm, and for an area c formed by the first curve 71, the ordinate, and the third curve 72, in an area c11 of a segment x∈(0,8), an applied false color may be a first color, and the corresponding FFR=0.8; in an area c12 of a segment x∈(8,24), an applied false color may be a second color, and the corresponding FFR=0.6; in an area c13 of a segment x∈(24,45), an applied false color may be a third color, and the corresponding FFR=0.54; in an area c14 of a segment x∈(45,78), an applied false color may be a fourth color, and the corresponding FFR=0.48. Certainly, in practical applications, there may be a color transition at the junction of two colors. This is not shown in FIG. 7 herein.

Therefore, the user needs to view only an image including the first coordinate system, such as FIG. 7, can intuitively see the thickness of the entire blood vessel, and can intuitively see the semi-diameter and FFR information of the two-dimensional section for any point on the blood vessel segment. For example, if the user is interested in the point at which x=10 mm, it can be learned, in the first coordinate system, that the semidiameter of the two-dimensional section of the blood vessel is 0.9 mm by using the first curve 71 or the third curve 72, and it can be determined that the FFR=0.6 of the blood vessel by using the second color. Therefore, it is convenient for the doctor user to diagnose a disease and determine a treatment plan.

Figure 8:
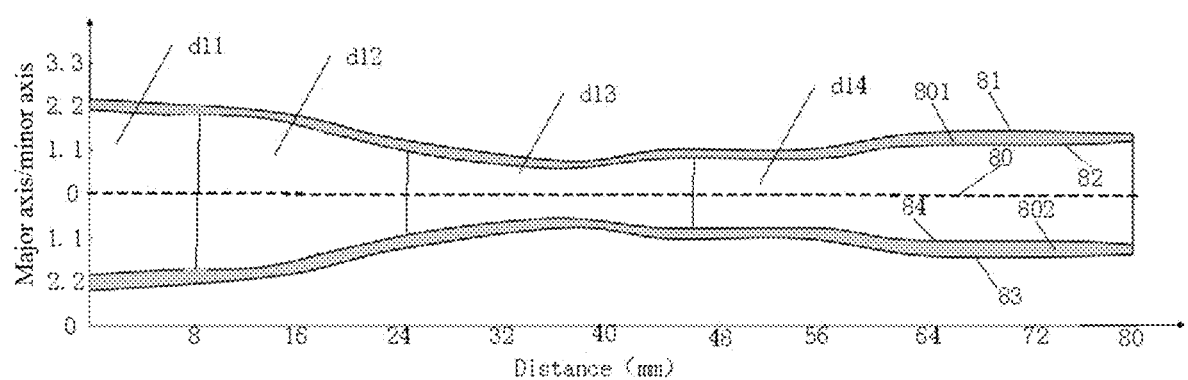
FIG. 8 is a schematic diagram of displaying a blood vessel image according to an embodiment of the present invention.

To facilitate the person skilled in the art to better understand and implement the present invention, FIG. 8 is another way of displaying a blood vessel image according to an embodiment of the present invention. As shown in FIG. 8, an abscissa represents a distance x, and an ordinate represents a major axis and a minor axis, and vital feature information is FFR information. A first sub-curve 81 or a third sub-curve 83 can both represent a correspondence between the distance x and the major axis. A second sub-curve 82 or a fourth sub-curve 84 can both represent a correspondence between the distance x and the minor axis. The first sub-curve 81 and the third sub-curve 83 are symmetrical with respect to an axis 80 parallel to the abscissa. The second sub-curve 82 and the fourth sub-curve 84 are symmetrical with respect to the axis 80 parallel to the abscissa. For an area d formed by the second sub-curve, the ordinate, and the fourth sub-curve, in an area d11 of a segment x∈(0,8), an applied false color may be a first color, and the corresponding FFR=0.8; in an area d12 of a segment x∈(8,24), an applied false color may be a second color, and the corresponding FFR=0.6; in an area d13 of a segment x∈(24,45), an applied false color may be a third color, and the corresponding FFR=0.54; in an area d14 of a segment x∈(45,78), an applied false color may be a fourth color, and the corresponding FFR=0.49. In addition, an area 801 between the first sub-curve 81 and the second sub-curve 82 and an area 802 between the third sub-curve 83 and the fourth sub-curve 84 are filled with gray. Similarly, FIG. 8 does not show too much the transition between the two colors. Therefore, the user needs to view only an image including the first coordinate system, such as FIG. 8. In this way, the doctor can diagnose a disease and determine a treatment plan relatively quickly.

In an embodiment of the present invention, the first coordinate system may further include: a third ordinate, the third ordinate represents vital feature information of each two-dimensional section, and an origin of the third ordinate is an intersection point of the abscissa and the third ordinate. On the basis of this first coordinate system, the vital feature information of the n two-dimensional sections of the blood vessel, the first curve, and the third curve are displayed in the same image in a mutual fusion manner. Specifically, for a preset number of points on the blood vessel segment, a fourth curve can be drawn according to the abscissa of the first coordinate system and the third ordinate, a mirror-symmetric curve of the fourth curve can be drawn as the fifth curve by using a straight line passing through the origin of the third ordinate and parallel to the abscissa is used as a central axis, and then the first curve, the third curve, the fourth curve and the fifth curve are displayed in the same image.

It should be noted that the third ordinate in this embodiment is not an additional ordinate that is different from the second ordinate, but is just a different name given to distinguish two different embodiments. The person skilled in the art can refer to the description of the embodiment shown in FIG. 5 to implement this embodiment. Details are not described herein.

In an embodiment of the present invention, in order to display the vital feature information of the n two-dimensional sections of the blood vessel, the first curve, and the third curve in the same image in a mutual fusion manner, for a preset number of points on the blood vessel segment, a false color is applied between two curves determined by the vital feature information of the n two-dimensional sections of the blood vessel and by the abscissa, where there is a mapping relationship between the false color and the vital feature information of the two-dimensional section, and the two curves are mirror-symmetric along the central axis. The person skilled in the art can refer to the description of the embodiment shown in FIG. 6 to implement this embodiment. Details are not described herein.

In order to improve the work efficiency of the doctor, in a specific implementation, a narrowest point on the blood vessel segment can further be displayed in the same image.

In a specific implementation, a distal point and a proximal point on the blood vessel segment where the vital feature information is within a preset threshold range may be further displayed in the same image, so that the work of the doctor can be further facilitated.

In a specific implementation, the same image may be a three-dimensional image. Specifically, for any two-dimensional section on the blood vessel segment, a false color may be applied to a vascular wall of the blood vessel, where there is a mapping relationship between the false color and the vital feature information of the two-dimensional section, that is, the blood vessel geometric structure information and the vital feature information of the blood vessel are displayed in a mutual fusion manner in the form of the three-dimensional image.

In order to improve the user experience, in a specific implementation, the image processing apparatus can further check, at a preset frequency, for example, every 10 s, whether a viewing instruction of a user is received, and when the viewing instruction of the user is received, display the blood vessel geometric structure information and vital feature information of the two-dimensional section of the blood vessel segment in which the user is interested. In other words, the user can click a point on the blood vessel segment of interest by using a mouse, and then the blood vessel geometric structure information and the vital feature information of the two-dimensional section corresponding to the point can be displayed on a display desktop at the same time.

Currently, for an ischemic heart disease, the conventional treatment method is mainly performing percutaneous coronary intervention (PCI) based on coronary angiography images to reconstruct the blood flow of the stenosis, to solve a downstream myocardium blood-supply problem. However, in fact, there is no fixed correspondence between whether myocardium is ischemia and the degree of vascular stenosis. Studies have shown that there is an error probability of one third between severity of stenosis judged by angiography and myocardial ischemia.

Figure 9:
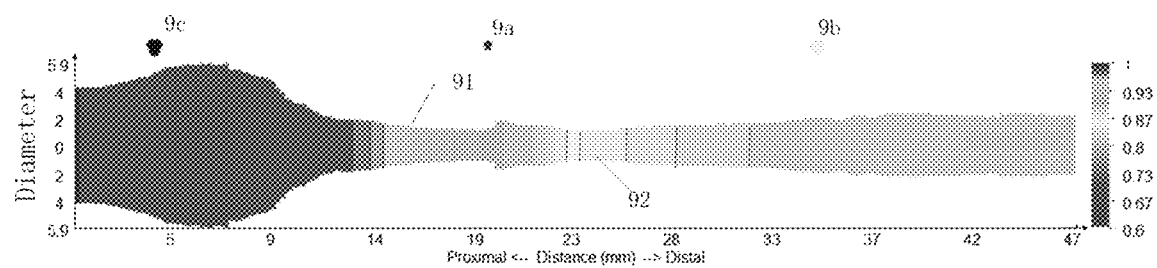
FIG. 9 is a schematic diagram of displaying a blood vessel image according to an embodiment of the present invention.
Figure 10:
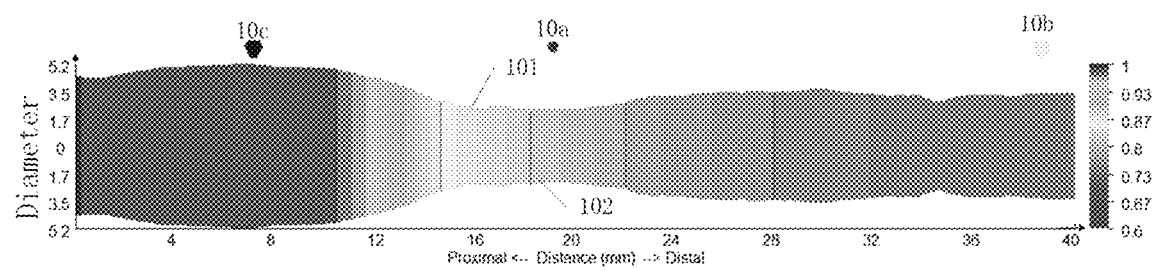
FIG. 10 is a schematic diagram of displaying a blood vessel image according to an embodiment of the present invention.

FIG. 9 and FIG. 10 each show a schematic diagram of displaying a blood vessel image by using the blood vessel image processing method in the embodiments of the present invention. In FIG. 9 and FIG. 10, a horizontal axis represents a distance x, a vertical axis represents a diameter, and a curve 91, a curve 92, a curve 101, and a curve 102 can all represent the change in the diameter with the distance x. The curve 91 and the curve 92 are mirror-symmetric to each other, and the curve 101 and the curve 102 are mirror-symmetric to each other. A mapping relationship between a false color and FFR information is shown on the right side of the coordinate system. In addition, a marking point 9*a* is used to display that a narrowest point on the blood vessel segment is x≈19 mm; a marking point 9*b* is used to display a distal point on the blood vessel segment where the vital feature information is within a preset threshold range is x≈35 mm; and a marking point 9*c* is sued to display that a proximal point on the blood vessel segment where the vital feature information is within the preset threshold range is x≈4 mm A marking point 10*a* is used to display that a narrowest point on the blood vessel segment is x≈17 mm; a marking point 10*b* is used to display that a distal point on the blood vessel segment where the vital feature information is within the preset threshold range is x≈38 mm; and a marking point 10*c* is used to show that a proximal point on the blood vessel segment where the vital feature information is within the preset threshold range is x≈7 mm.

In addition, for areas formed by mirror-symmetric curves and ordinates, different areas divided by vertical lines in FIG. 9 and FIG. 10 have different false colors, and the vertical lines correspond to the vertical bars identified in FIG. 9 and FIG. 10. The person skilled in the art can refer to the foregoing implementation to apply a false color. Details are not described herein. Referring to FIG. 9, it can be learned that the degree of blood vessel stenosis is high, but FFR is negative, that is, the FFR information higher than 0.8. However, in the industry, the blood vessel with the FFR information higher than 0.8 has a low degree of vascular lesion, and it indicates that the myocardium is not ischemic. Referring to FIG. 10, it can be learned that the degree of vascular stenosis is low, but the FFR is positive, that is, the FFR information is lower than 0.8, it indicates that the myocardium is ischemia, and subsequent treatments such as stent placement may be required.

In conclusion, in the blood vessel image processing method provided by the embodiment of the present invention, an association relationship between the blood vessel geometric structure information and the vital feature information is established, and then the blood vessel geometric structure information and the vital feature information are displayed in the same image in a mutual fusion manner by using the association relationship as a reference. A user of the blood vessel image processing apparatus, especially a doctor user, can directly and simultaneously see vital feature information and blood vessel geometric structure information of any one of the n two-dimensional sections by viewing an image. There is no need for the doctor to compare two images that are a first image and a second image to view the vital feature information and the blood vessel geometric structure information of any point or two-dimensional section of the blood vessel segment. Therefore, it is convenient for the doctor user to diagnose a disease of a patient, and it is further convenient for the doctor user to determine a treatment plan of the disease. In this way, work efficiency of the user can be improved.

Figure 11:
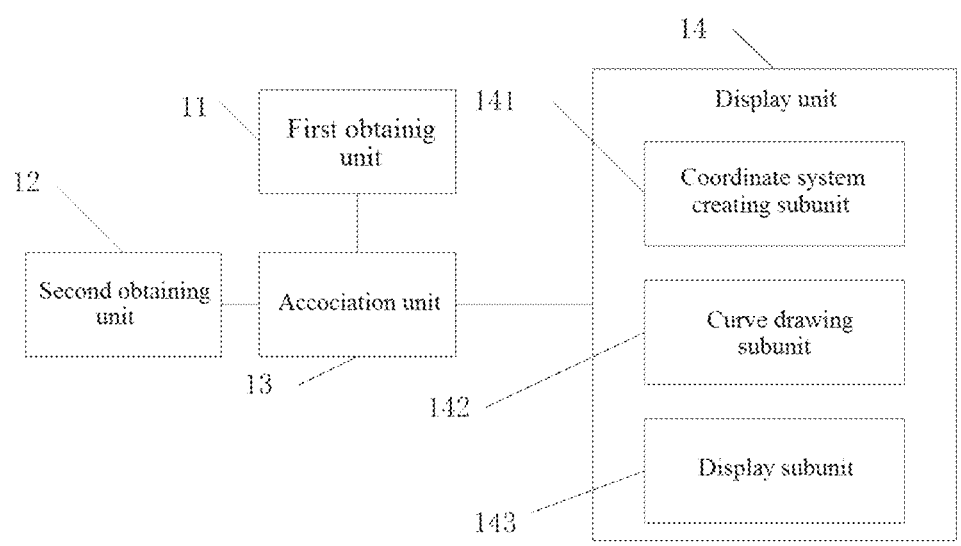
FIG. 11 is a schematic structural diagram of a blood vessel image processing apparatus according to an embodiment of the present invention.

In order to enable the person skilled in the art to better understand and implement the present invention, FIG. 11 is a blood vessel image processing apparatus according to an embodiment of the present invention. The blood vessel image processing apparatus may include: a first obtaining unit 11, a second obtaining unit 12, an association unit 13, and a display unit 14.

The first obtaining unit 11 can obtain blood vessel geometric structure information of a blood vessel segment of interest. The second obtaining unit 12 can obtain vital feature information of the blood vessel segment.

The association unit 13 may establish an association relationship between the blood vessel geometric structure information and the vital feature information.

The display unit 14 may display the blood vessel geometric structure information and the vital feature information in the same image in a mutual fusion manner by using the association relationship as a reference.

In a specific implementation, the association unit 13 may set a reference position, and associate the vital feature information in the blood vessel segment with the blood vessel geometric structure information according to the reference position. The blood vessel includes n two-dimensional sections, the n two-dimensional sections correspond to n points on the blood vessel, and the reference position includes one of the following: a reference point, a reference section or a reference line.

It should be noted that the blood vessel may include n two-dimensional sections, the n two-dimensional sections correspond to n points on the blood vessel segment, and the information blood vessel geometric structure information includes at least: blood vessel geometric structure information of each two-dimensional section of the blood vessel. For ease of description, a distance from the corresponding point on the blood vessel segment to the preset reference point on the blood vessel segment can be referred to as x, $n \geq 1$, $y \geq x \geq 0$, and y represents a length of the blood vessel of interest.

In a specific implementation, the display unit 14 may display the vital feature information of the n two-dimensional sections of the blood vessel, the blood vessel geometric structure information of the n two-dimensional sections of the blood vessel, and the distance x from the point corresponding to each two-dimensional section to the preset reference point on the blood vessel segment in the same image in a mutual fusion manner.

In a specific implementation, the display unit 14 may include: a coordinate system creating subunit 141. The coordinate system establishing subunit 141 may create a first coordinate system. An abscissa of the first coordinate system represents a distance x from a point on the blood vessel segment to the preset reference point on the blood vessel segment, a first ordinate of the first coordinate system represents blood vessel geometric structure information of each two-dimensional section, and an origin of the first ordinate is an intersection point of the abscissa and the first ordinate. A curve drawing subunit 142 can determine, for a preset number of two-dimensional sections of the blood vessel segment, that is, a preset number of sampling points on the blood vessel, a corresponding point according to the abscissa and the first ordinate of the first coordinate system, and draw a first curve according to the determined point. The display subunit 143 can display the vital feature information of the n two-dimensional sections of the blood vessel and the first curve in the same image in a mutual fusion manner.

In a specific implementation, the display subunit 143 may apply a false color to an area between the first curve, the abscissa and the first ordinate of the first coordinate system for a preset number of points on the blood vessel segment, where there is a mapping relationship between the false color and the vital feature information of the two-dimensional section; and display the first curve, the false-colored area, and the first coordinate system in the same image.

In a specific implementation, the first coordinate system further includes: a second ordinate. The second ordinate represents vital feature information of each two-dimensional section, and an origin of the second ordinate is an intersection point of the abscissa and the second ordinate. The display subunit 143 may determine a corresponding point according to the abscissa of the first coordinate system and the second ordinate for a preset number of two-dimensional sections of the blood vessel segment, that is, a preset number of sampling points on the blood vessel, and draw a second curve according to the determined point; and display the first curve, the second curve, and the first coordinate system in the same image.

In a specific implementation, the display subunit 143 may apply a false color to a curve determined by the vital feature information of the n two-dimensional sections of the blood vessel and the abscissa, where there is a mapping relationship between the false color and the vital feature information of the two-dimensional section; and display the first curve, the false-colored curve determined by the vital feature information of the n two-dimensional sections of the blood vessel and the abscissa, and the first coordinate system in the same image.

In a specific implementation, the display subunit 143 may also use a straight line passing through the origin of the first ordinate and parallel to the abscissa as a central axis to draw a mirror-symmetric curve of the first curve, as a third curve. A longitudinal distance from the abscissa to the third curve is not less than zero. The display subunit 143 may further display the vital feature information of the n two-dimensional sections of the blood vessel, the first curve, and the third curve in the same image in a mutual fusion manner.

In a specific implementation, the display subunit 143 may apply a false color to an area between the first curve, the third curve, and the first ordinate for a preset number of points on the blood vessel segment, where there is a mapping relationship between the false color and the vital feature information of the two-dimensional section; and display the first curve, the third curve, the false-colored area, and the first coordinate system in the same image.

In a specific implementation, the first coordinate system further includes: a third ordinate. The third ordinate represents vital feature information of each two-dimensional section, and an origin of the third ordinate is an intersection point of the abscissa and the third ordinate. The curve drawing subunit 142 may further draw a fourth curve according to the abscissa of the first coordinate system and the third ordinate for a preset number of points on the blood vessel segment; and draw a mirror-symmetric curve of the fourth curve as a fifth curve by using a straight line passing through the origin of the third ordinate and parallel to the abscissa as a central axis. The display subunit 143 can display the first curve, the third curve, the fourth curve and the fifth curve in the same image.

In a specific implementation, the display subunit 143 may apply, for a preset number of points on the blood vessel segment, a false color to two curves determined by the vital feature information of the n two-dimensional sections of the blood vessel and the abscissa. There is a mapping relationship between the false color and the vital feature information of the two-dimensional section, and the two curves are mirror-symmetric along the central axis.

In a specific implementation, the blood vessel geometric structure information of each two-dimensional section of the blood vessel includes at least one of the following: a diameter, a semidiameter, a cross-sectional area, or a major axis and a minor axis; and/or, the two-dimensional section of the blood vessel is a tangential section of the blood vessel; and/or, the vital feature information of each two-dimensional section of the blood vessel includes at least one of the following: FFR information, a ratio of a distal pressure of the blood vessel to a proximal pressure or a pressure value; and/or, the blood vessel is a heart blood vessel, a peripheral blood vessel, or a cerebral blood vessel.

In a specific implementation, the display subunit 143 may further fill an area between curves corresponding to the major axis and the minor axis with a preset color when the blood vessel geometric structure information of each two-dimensional section of the blood vessel is the major axis and the minor axis; and/or, the display subunit 143 may further display a narrowest point on the blood vessel segment in the same image; and/or, display, in the same image, a distal point and a proximal point of the blood vessel segment where the vital feature information is within a preset threshold range.

In a specific implementation, the same image is a three-dimensional image, and the display unit 14 may apply a false color to a lumen wall of the blood vessel for any two-dimensional section on the blood vessel segment, where there is a mapping relationship between the false color and the vital feature information of the two-dimensional section.

In a specific implementation, the image processing apparatus may further include: a checking unit (not shown) that can check whether a viewing instruction of a user is received. The display unit 14 can further display the blood vessel geometric structure information and vital feature information of the two-dimensional section on the blood vessel segment in which the user is interested when the checking unit receives the viewing instruction of the user.

In a specific implementation, the second obtaining unit 12 can obtain a coronary angiography image or tomographic image of the blood vessel; perform image processing on the coronary angiography image or the tomographic image of the blood vessel, where the image processing process at least includes image segmentation and vascular lumen morphology reconstruction; perform calculation on the vascular lumen morphology after segmentation and reconstruction to obtain the blood vessel geometric structure information at each position of the reconstructed blood vessel, and obtain the vital feature information of each two two-dimensional section by using a blood vessel pressure difference or a FFR calculation algorithm. In addition, there may be multiple specific imaging manners and principles, such as an X-ray imaging principle, a CT imaging principle, an intravascular ultrasound imaging principle, or an optical coherence tomography imaging principle.

In a specific implementation, the second obtaining unit 12 may: use a guide wire or a catheter with a pressure sensor and a positioning component to obtain the vital feature information of the points on the blood vessel segment of interest. The vital feature information of each position point corresponds to the two-dimensional section of the blood vessel of interest.

The embodiment of the present invention provides a computer storage medium on which a computer program that can be run on a processor is stored, and when the computer program is executed by the processor, the blood vessel image processing method according to any one of possible implementations can be implemented.

An embodiment of the present invention further provides an imaging device, and the imaging device may include any one of the above blood vessel image processing apparatuses. In addition, the imaging device may further include other components for implementing imaging processing.

In a specific implementation, the imaging device may include multiple types of devices. The imaging device may be an angiography machine, or may be an intravascular ultrasound imaging device, or may be an optical coherence tomography imaging device, or may be an X-ray computed tomography (Computed Tomography, CT) camera.

According to one or more embodiments, the storage medium may include a computer-readable recording/storage medium, such as a random access memory (RAM), a read only memory (ROM), a flash memory, an optical disk, a magnetic disk, a solid state disk, etc. According to one or more embodiments, the controller is executed by a microprocessor programmed to perform one or more operations and/or functions described herein. According to one or more embodiments, the controller is executed in whole or in part by specially configured hardware, for example, executed by one or more dedicated integration or ASIC(s).

In conclusion, the above embodiments provided by the present invention are only illustrative of the principles and effects of the present invention, and are not used to limit the present invention. Anyone familiar with this technology can modify or change the above embodiments without departing from the spirit and scope of the present invention. Therefore, all equivalent modifications or changes made by the person with ordinary knowledge in the technical field without departing from the spirit and technical ideas disclosed in the present invention should still be covered by the claims of the present invention.

The invention claimed is:

1. A blood vessel image processing method, comprising:
obtaining blood vessel geometric structure information of a blood vessel segment of interest, the blood vessel geometric structure information of the blood vessel segment including at least a major axis and a minor axis;
obtaining vital feature information of the blood vessel segment;
establishing an association relationship between the blood vessel geometric structure information and the vital feature information, comprising:
setting a reference position, and associating the vital feature information in the blood vessel segment with the blood vessel geometric structure information according to the reference position;
wherein the blood vessel comprises n two-dimensional sections, the n two-dimensional sections correspond to n points on the blood vessel segment, and the reference position comprises one of the following: a reference point, a reference section or a reference line, n≥1, and n is a positive integer
making a correspondence between the vital feature information of each of the n points on the blood vessel segment according to a position sensor; and
displaying the blood vessel geometric structure information and the vital feature information in the same image in a mutual fusion manner by using the association relationship as a reference comprising:

establishing a first coordinate system, wherein an abscissa of the first coordinate system indicates a distance from a point on the blood vessel segment to a preset reference position on the blood vessel segment, a first ordinate of the first coordinate system indicates blood vessel geometric structure information of a blood vessel two-dimensional section corresponding to a point on the blood vessel segment, and an origin of the first ordinate is an intersection point of the abscissa and the first ordinate, wherein the two-dimensional section of the blood vessel is a tangential section of the blood vessel;

for a preset number of two-dimensional sections of the blood vessel segment, determining a corresponding point according to the abscissa and the first ordinate of the first coordinate system, and connecting the corresponding point according to the determined point to draw a first curve, the first curve comprising a first sub-curve and a second sub-curve, wherein the first sub-curve represents a correspondence between a distance and the major axis of the blood vessel geometric structure information of the blood vessel segment, and the second sub-curve represents a correspondence between the distance and the minor axis of the blood vessel geometric structure information of the blood vessel segment;

applying a false color to an area between the second sub-curve, the abscissa and the ordinate of the first coordinate system, wherein there is a mapping relationship between the false color and the vital feature information of the two-dimensional section; and displaying, in the same image:
the first sub-curve, the second sub-curve, the false-colored area and the first coordinate system, and a distal point and a proximal point of the blood vessel segment where the vital feature information is within a preset threshold.

2. The blood vessel image processing method according to claim 1, comprising:

drawing a mirror-symmetric curve of the first curve as a third curve by using a straight line passing through the origin of the first ordinate and parallel to the abscissa as a central axis; wherein a longitudinal distance from the abscissa to the third curve is not less than zero; and displaying the vital feature information in the blood vessel segment, the first curve, and the third curve in the same image in a mutual fusion manner.

3. The blood vessel image processing method according to claim 2, wherein the first coordinate system further comprises: a third ordinate, and the third ordinate represents vital feature information of each two-dimensional section, and an origin of the third ordinate is an intersection point of the abscissa and the third ordinate;

the displaying the vital feature information in the blood vessel segment, the first curve, and the third curve in the same image in a mutual fusion manner comprises:

for a preset number of points on the blood vessel segment, drawing a fourth curve according to the abscissa of the first coordinate system and the third ordinate;

drawing a mirror-symmetric curve of the fourth curve as a fifth curve by using a straight line passing through the origin of the third ordinate and parallel to the abscissa as a central axis; and displaying the first curve, the third curve, the fourth curve, and the fifth curve in the same image.

4. The blood vessel image processing method according to claim 1, wherein the vital feature information of each two-dimensional section of the blood vessel comprises at least one of the following: FFR information, a ratio of a distal pressure of the blood vessel to a proximal pressure, or a pressure value; and/or, the blood vessel is a heart blood vessel, a peripheral blood vessel or a cerebral blood vessel.

5. The blood vessel image processing method according to claim 4, further comprising:

filling an area between curves corresponding to the major axis and the minor axis with a preset color; and/or, displaying a narrowest point on the blood vessel segment in the same image.

6. The blood vessel image processing method according to claim 1, further comprising:

checking whether a viewing instruction of a user is received; and when the viewing instruction of the user is received, displaying the blood vessel geometric structure information and the vital feature information of the two-dimensional section of the blood vessel segment in which the user is interested.

7. The blood vessel image processing method according to claim 1, wherein the obtaining vital feature information of a blood vessel segment of interest comprises:

obtaining a coronary angiography image or a tomographic image of the blood vessel segment;

performing image processing on the coronary angiography image or the tomographic image of the blood vessel segment, wherein the image processing process at least comprises image segmentation and vascular lumen morphology reconstruction; and performing calculation on the vascular lumen morphology after segmentation and reconstruction to obtain the blood vessel geometric structure information of a lumen at each position on the reconstructed blood vessel segment, and obtaining vital feature information corresponding to each two-dimensional section by using a blood vessel pressure difference or a FFR calculation algorithm.

8. A blood vessel image processing apparatus, comprising:

a first obtaining unit, configured to obtain blood vessel geometric structure information of a blood vessel segment of interest, the blood vessel geometric structure information of the blood vessel segment including at least a major axis and a minor axis;

a second obtaining unit, configured to obtain vital feature information of the blood vessel segment;

an association unit, configured to establish an association relationship between the blood vessel geometric structure information and the vital feature information, the association unit configured to:

set a reference position, and associate the vital feature information in the blood vessel segment with the blood vessel geometric structure information according to the reference position;

wherein the blood vessel comprises n two-dimensional sections, the n two-dimensional sections correspond to n points on the blood vessel segment, and the reference position comprises one of the following: a reference point, a reference section or a reference line, n≥1, and n is a positive integer make a correspondence between the vital feature information of each of the n points on the blood vessel segment according to a position sensor; and a display unit, configured to display the blood vessel geometric structure information and the vital feature information in the same image in a mutual fusion manner based using the association relationship a reference, the display unit configured to:

establish a first coordinate system, wherein an abscissa of the first coordinate system indicates a distance from a point on the blood vessel segment to a preset reference position on the blood vessel segment, a first ordinate of the first coordinate system indicates blood vessel geometric structure information of a blood vessel two-dimensional section corresponding to a point on the blood vessel segment, and an origin of the first ordinate is an intersection point of the abscissa and the first ordinate, wherein the two-dimensional section of the blood vessel is a tangential section of the blood vessel;

for a preset number of two-dimensional sections of the blood vessel segment, determine a corresponding point according to the abscissa and the first ordinate of the first coordinate system, and connecting the corresponding point according to the determined point to draw a first curve, the first curve comprising a first sub-curve and a second sub-curve, wherein the first sub-curve represents a correspondence between a distance and the major axis of the blood vessel geometric structure information of the blood vessel segment, and the second sub-curve represents a correspondence between the distance and the minor axis of the blood vessel geometric structure information of the blood vessel segment apply a false color to an area between the second sub-curve, the abscissa and the ordinate of the first coordinate system, wherein there is a mapping relationship between the false color and the vital feature information of the two-dimensional section; and display, in the same image:

the first sub-curve, the second sub-curve, the false-colored area and the first coordinate system, and a distal point and a proximal point of the blood vessel segment where the vital feature information is within a preset threshold.

9. The blood vessel image processing apparatus according to claim 8, wherein the display subunit is further configured to draw a mirror-symmetric curve of the first curve as a third curve by use a straight line passing through the origin of the first ordinate and parallel to the abscissa as a center axis; wherein a longitudinal distance from the abscissa to the third curve is not less than zero; and the display subunit is further configure to display the vital feature information of the n two-dimensional sections of the blood vessel, the first curve, and the third curve in the same image in a mutual fusion manner.

10. The blood vessel image processing apparatus according to claim 9, wherein the first coordinate system further comprises: a third ordinate, the third ordinate represents vital feature information of each two-dimensional section, and an origin of the third ordinate is an intersection point of the abscissa and the third ordinate;

the curve drawing subunit is further configured to draw a fourth curve according to the abscissa of the first coordinate system and the third ordinate for a preset number of points on the blood vessel segment; and draw a mirror-symmetric curve of the fourth curve as a fifth curve by using a straight line passing through the origin of the third ordinate and parallel to the abscissa as a central axis; and the display subunit is configured to display the first curve, the third curve, the fourth curve and the fifth curve in the same image.

11. The blood vessel image processing apparatus according to claim 8, wherein the display subunit is further configured to: fill an area between curves corresponding to the major axis and the minor axis with a preset color; and/or, the display subunit is further configured to: display a narrowest point on the blood vessel segment in the same image.

12. The blood vessel image processing apparatus according to claim 8, further comprising:

a checking unit, configured to check whether a viewing instruction of a user is received; wherein the display unit is further configured to display the blood vessel geometric structure information and the vital feature information of the two-dimensional section of the blood vessel segment in which the user is interested when the checking unit receives the viewing instruction of the user.

13. The blood vessel image processing apparatus according to claim 8, wherein the second obtaining unit is configured to:

obtain a coronary angiography image or a tomographic image of the blood vessel; perform image processing on the coronary angiography image or the tomographic image of the blood vessel, wherein the image processing process comprises at least image segmentation and vascular lumen morphology reconstruction; perform calculation on the vascular lumen morphology after segmentation and reconstruction to obtain the vascular geometric structure information of a lumen at each position of the reconstructed blood vessel, and obtain the vital feature information corresponding to each two-dimensional section by using a blood vessel pressure difference or a FFR calculation algorithm.

14. A computer storage medium on which a computer program that can be run on a processor is stored, wherein the computer program implements the blood vessel image processing method according to claim 1 when being executed by the processor.

15. An imaging device, comprising the blood vessel image processing apparatus according to claim 8.

16. The imaging device according to claim 15, comprising any one of the following: an angiography machine, an X-ray tomography camera, an intravascular ultrasound imaging device, and an optical coherence tomography imaging device.

* * * * *